(12) United States Patent
Coco et al.

(10) Patent No.: US 7,084,246 B2
(45) Date of Patent: Aug. 1, 2006

(54) EPIDERMAL GROWTH FACTOR AGONISTS

(75) Inventors: Wayne M. Coco, Cologne (DE); Philip P. Pienkos, The Woodlands, TX (US); A. Katrina Loomis, Houston, TX (US)

(73) Assignee: Molecular Logix, Inc., The Woodlands, TX (US)

(*) Notice: Subject to any disclaimer, the term of this patent is extended or adjusted under 35 U.S.C. 154(b) by 34 days.

(21) Appl. No.: 10/820,640

(22) Filed: Apr. 8, 2004

(65) Prior Publication Data

US 2005/0032162 A1  Feb. 10, 2005

Related U.S. Application Data

(60) Provisional application No. 60/463,890, filed on Apr. 17, 2003.

(51) Int. Cl.
*A61K 38/18* (2006.01)
*C07K 14/485* (2006.01)
*C07K 5/00* (2006.01)

(52) U.S. Cl. .................. 530/324; 424/85.1; 514/12
(58) Field of Classification Search ............... None
See application file for complete search history.

(56) References Cited

U.S. PATENT DOCUMENTS

| | | | |
|---|---|---|---|
| 5,102,789 A | | 4/1992 | Siegel et al. |
| 5,194,596 A | * | 3/1993 | Tischer et al. ............ 530/399 |
| 5,350,836 A | * | 9/1994 | Kopchick et al. ......... 530/399 |

OTHER PUBLICATIONS

Coco WM, et al., Growth factor engineering by degenerate homoduplex gene family recombination. Nat Biotechnology. Dec 2002;20(12):1246-50. Epub Nov. 11, 2002.*
Bowie, et al., Deciphering the message in protein sequences: tolerance to amino acid substitutions.Science. Mar. 16, 1990;247(4948):1306-10.*
Wells et al., Additivity of mutational effects in proteins. Biochemistry. Sep. 18, 1990;29(37):8509-17.*
Ngo et al., The Protein Folding Problems and Teritary Structure Prediction, Merz et al., eds, Birkhauser, Boston, pp. 14-16.*
Benjamin et al., 1998, Development 125:1591-1598.*
Vukicevic et al. 1996, PNAS USA 93:9021-9026.*
Massague. 1987, Cell 49:437-8.*
Pilbeam et al., 1993, Bone 14:717-720.*
Skolnick et al. 2000, Trends in Biotech. 18:34-39.*
Bork. 2000, Genome Research 10:398-400.*
Doerks et al. 1998, Trends in Genetics 14:248-250.*
Smith et al. 1997, Nature Biotechnology 15:1222-1223.*
Brenner. 1999 Trends in Genetics 15:132-133.*
Bork et al. 1996, Trends in Genetics 12:425-427.*
U.S. Appl. No. 11/172,611, filed Jun. 30, 2005, Pienkos et al.
U.S. Appl. No. 11/172,610, filed Jun. 30, 2005, Bishop et al.

* cited by examiner

*Primary Examiner*—Brenda Brumback
*Assistant Examiner*—Cherie M. Woodward
(74) *Attorney, Agent, or Firm*—Elmore Patent Law Group, PC; Carolyn S. Elmore; Darlene A. Vanstone

(57) ABSTRACT

The present invention features polypeptides that have at least 90% amino acid identity to wild-type epidermal growth factor, and also have epidermal growth factor biological activity that is greater than the biological activity of wild-type epidermal growth factor.

1 Claim, 8 Drawing Sheets

SEQ ID NO: 1

NSDSECPLSHDGYCLHDGVCMYIEALDKYACNCVVGYIGERCQYRDLKWW
ELR

FIG. 1

SEQ ID NO: 2

AsnSerAspSerGlyCysProSerPheHisAspGlyTyr
CysLeuAsnGlyGlyValCysMETTyrIleGluAlaLeu
AspLysTyrAlaCysAsnCysValIleGlyTyrAsnGly
AspArgCysGlnThrArgAspLeuLysTrpTrpGluLeu
Arg

FIG. 2

SEQ ID NO: 3

AATAGTGATTCTGGATGTCCCTCGTTCCATGATGGGTACTGCCTCAATGGT
GGTGTGTGCATGTATATTGAAGCATTGGACAAGTATGCATGCAACTGTGTT
ATTGGCTACAACGGGGATCGATGTCAGACTCGAGACCTGAAGTGGTGGGA
ACTGCGC

FIG. 3

EPIDERMAL GROWTH FACTOR AGONISTS

RELATED APPLICATION

This application claims the benefit of U.S. Provisional Application No. 60/463,890, filed on Apr. 17, 2003. The entire teachings of the above application is incorporated herein by reference.

BACKGROUND OF THE INVENTION

Epidermal growth factor (EGF) is a 53 amino acid cytokine which is proteolytically cleaved from a large integral membrane protein precursor. EGF has been shown to stimulate growth of epithelial cells, accelerate tooth eruption and eyelid opening in mice, inhibit gastric acid secretion, provide gastrointestinal mucosal protection, and promote wound healing and corneal regeneration through growth and differentiation of cells. EGF is made by ectodermal cells, monocytes, kidney cells, and duodenal glands.

Since EGF has a number of therapeutic uses, methods and compounds that result in increased EGF biological activity in a cell or individual would be advantageous.

SUMMARY OF THE INVENTION

The present invention features EGF agonists that have increased EGF biological activity compared to wild-type EGF polypeptides. These EGF agonists are polypeptides that have amino acid identity to EGF, and increased EGF biological activity. Such polypeptides, and nucleic acids encoding these polypeptides can be used therapeutically in situations in which EGF is indicated.

In one aspect, the present invention features an epidermal growth factor (EGF) polypeptide having at least 90% amino acid identity to SEQ ID NO: 1 and having epidermal growth factor biological activity that is greater than the biological activity of the polypeptide of SEQ ID NO: 1 (human wild-type EGF). In one embodiment, the EGF polypeptide has the amino acid sequence of SEQ ID NO: 2. In embodiments, the EGF polypeptide has EGF biological activity that is at least two times, at least five times, at least ten times, at least twenty-five times, at least fifty times, or at least one hundred times greater than the biological activity of the polypeptide of SEQ ID NO: 1.

In another aspect, the invention features an isolated nucleic acid molecule that encodes an epidermal growth factor (EGF) polypeptide having at least 90% amino acid identity to SEQ ID NO: 1 and having epidermal growth factor biological activity that is greater than the biological activity of the polypeptide of SEQ ID NO: 1. In one embodiment, the nucleic acid molecule has the sequence of SEQ ID NO: 3.

In other aspects, the present invention features vectors comprising the isolated epidermal growth factor polypeptide described above, a cell comprising the vector, and a cell comprising the isolated epidermal growth factor described above. The present invention also features a cell comprising the polypeptide of the present invention and a cell capable of secreting the polypeptide of the present invention.

The present invention also features a method of treating a condition characterized by EGF biological activity, comprising administering an epidermal growth factor (EGF) polypeptide having at least 90% amino acid identity to SEQ ID NO: 1 and having epidermal growth factor biological activity that is greater than the biological activity of the polypeptide of SEQ ID NO: 1.

BRIEF DESCRIPTION OF THE DRAWINGS

FIG. 1 shows the amino acid sequence of human wild-type epidermal growth factor polypeptide in its mature form (SEQ ID NO: 1).

FIG. 2 shows the amino acid sequence of the EGF0021 polypeptide (SEQ ID NO: 2).

FIG. 3 shows the DNA sequence encoding the EGF0021 polypeptide (SEQ ID NO: 3).

DETAILED DESCRIPTION OF THE INVENTION

Figure 4A:
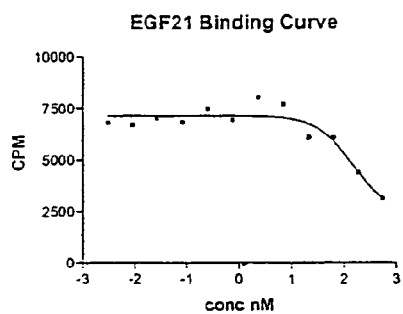
FIG. 4A is a graph of the displacement of $^{125}$I labeled-EGF from EGF receptors (counts per minute (cpm)) by various concentrations of EGF0021 (log [conc. nM]).

A description of preferred embodiments of the invention follows.

The present invention features polypeptides having at least 90% amino acid identity to the polypeptide sequence of SEQ ID NO: 1 (human wild-type EGF polypeptide) and having epidermal growth factor biological activity that is greater than the biological activity of the polypeptide of SEQ ID NO: 1. As described herein, such polypeptides can act as "super agonists." These polypeptides bind to the EGF receptor and per molecule bound to EGF receptor, have increased EGF biological activity compared to human wild-type EGF polypeptide. Such polypeptides possess a number of useful properties. For example, the polypeptides of the present invention can be used in circumstances in which EGF is normally used, such as in wound healing, growth and differentiation of corneal tissue, and treatment of chronic gastric mucosal pathologies.

Polypeptides

The present invention features polypeptides having at least 90% amino acid identity to the EGF polypeptide of SEQ ID NO: 1 (mature biologically active human wild-type EGF polypeptide) and having epidermal growth factor biological activity that is greater than the biological activity of the polypeptide of SEQ ID NO: 1. As used herein, the term "polypeptide" refers to a polymer of amino acids, and not to a specific length; thus, peptides, oligopeptides and proteins are included within the definition of a polypeptide. In one embodiment, the polypeptide of the present invention has the amino acid sequence of SEQ ID NO: 2. In another embodiment, the polypeptide of the present invention is encoded by the nucleic acid sequence of SEQ ID NO: 3.

Preferably the polypeptides of the present invention are "isolated," "substantially pure," or "substantially pure and isolated," which occurs when the polypeptide is substantially free of cellular material, when it is isolated from recombinant and non-recombinant cells, or is free of chemical precursors or other chemicals when it is chemically synthesized. In addition, the polypeptides of the present invention can be joined to another polypeptide with which it is not normally associated in a cell (e.g., in a "fusion protein") and still be "isolated" "substantially pure," or "substantially pure and isolated." An isolated, substantially pure, or substantially pure and isolated polypeptide may be obtained, for example using affinity purification techniques described herein, as well as other techniques described herein and known to those skilled in the art.

As described above, the polypeptides of the present invention have epidermal growth factor biological activity that is greater than the biological activity of the polypeptide of SEQ ID NO: 1. By "epidermal growth factor biological activity" means that a protein has one or more activities of the polypeptide of SEQ ID NO: 1 (human wild-type EGF). For example, the biological activity can be activation of the EGF receptor, which can be assayed using any of a number of known assays, for example, measurement of proliferation of a cell sample, for example, proliferation of epithelial cells or epidermal cells in the presence of the polypeptide compared to the proliferation of the cells in the absence of the polypeptide. In another method, phosphorylation of the EGF receptor or activation of a downstream signaling target of the EGF receptor can be used to detect EGF receptor activation. The polypeptide of the present invention preferably has epidermal growth factor biological activity that is at least two times, five times, ten times, twenty-five times, fifty times, or one hundred times greater than the biological activity of the polypeptide of SEQ ID NO: 1. This biological activity can be assessed by measuring the biological activity of a candidate polypeptide using any method described herein or any other suitable method, and comparing it to the biological activity of the polypeptide having the amino acid sequence of SEQ ID NO: 1.

As described above, the polypeptides of the present invention have at least 90% sequence identity to the amino acid sequence of SEQ ID NO: 1, and has a biological activity of an EGF polypeptide. In other embodiments, the polypeptides of the present invention have at least 91%, at least 92%, at least 93%, at least 94%, at least 95% at least 96%, at least 97%, or at least 98% amino acid identity to the amino acid sequence of SEQ ID NO: 1, and has a biological activity of an EGF polypeptide. The percent identity of two nucleotide or amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions× 100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence (FIG. 1). The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the BLASTN and BLASTX programs (version 2.2) as described in Schaffer et al., *Nucleic Acids Res.* 29:2994–3005 (2001). When utilizing BLAST and Gapped BLAST programs, the default parameters of the respective programs (e.g., BLASTN) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM 120 weight residue table, a gap length penalty of 12, and a gap penalty of 4 can be used. Additional algorithms for sequence analysis are known in the art and include ADVANCE and ADAM as described in Torellis and Robotti, *Comput. Appl. Biosci.*, 10:3–5 (1994); and FASTA described in Pearson and Lipman, *Proc. Natl. Acad. Sci. USA*, 895: 2444–2448 (1988).

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In other embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The polypeptides of the present invention can be generated using any number of methods. Amino acids that contribute to the biological activity of an EGF polypeptide can be identified by methods known in the art, such as site directed mutagenesis or alanine-scanning mutagenesis (Cunningham et al., *Science*, 244:1081–1085 (1989)). The latter procedure introduces a single alanine mutation at each of the residues in the molecule (one mutation per molecule). The resulting mutant molecules are then tested for biological activity of an EGF polypeptide in vitro. Alternatively, the polypeptides of the present invention can be generated using other methods for mutagenesis, for example, DNA shuffling techniques, which are known in the art, and the polypeptides can be tested for EGF biological activity.

The present invention also provides chimeric or fusion polypeptides. These polypeptides comprise a polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment, the fusion polypeptide does not affect the function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example, β-galactosidase fusions, yeast two-hybrid GAL fusions, poly-His fusions, and Ig fusions. Such fusion polypeptides, particularly poly-His fusions, can facilitate the purification of recombinant polypeptide, for example, as described herein. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhands between two consecutive nucleic acid fragments that can subsequently be annealed and re-amplified to generate a chimeric nucleic acid sequence (see Ausubel et al., "Current Protocols in Molecular Biology," John Wiley & Sons, (1998), the entire teachings of which are incorporated by reference herein). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

Nucleic Acids

The present invention also features isolated nucleic acid molecules encoding a polypeptide have at least 90%, at least 91%, at least 92%, at least 93%, at least 94%, at least 95%, at least 96%, at least 97%, or at least 98% amino acid identity to the amino acid sequence of SEQ ID NO: 1, and having epidermal growth factor biological activity that is greater than the biological activity of the polypeptide of SEQ ID NO: 1. In one embodiment, the nucleic acid molecule has the nucleic acid sequence of SEQ ID NO: 3.

The isolated nucleic acid molecules of the present invention can be RNA, for example, mRNA, or DNA. DNA molecules can be double-stranded or single-stranded. The nucleic acid molecule can also be fused to a marker sequence, for example, a sequence that encodes a polypeptide to assist in isolation or purification of the polypeptide. Such sequences include, but are not limited to, those that encode a glutathione-S-transferase (GST) fusion protein, those that encode a hemagglutinin A (HA) polypeptide marker from influenza, and sequences encoding a His tag.

An "isolated," "substantially pure," or "substantially pure and isolated" nucleic acid molecule, as used herein, is one that has been completely or partially purified from other nucleic acid sequences (e.g., as in a nucleic acid library). For example, an isolated nucleic acid of the invention may be substantially isolated with respect to culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50%, 80%, or 90% (on a molar basis) of all macromolecular species present.

The nucleic acid molecules of the present invention can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. An isolated nucleic acid molecule or nucleotide sequence can include a nucleic acid molecule or nucleotide sequence that is synthesized chemically or by recombinant means. Therefore, recombinant DNA contained in a vector are included in the definition of "isolated" as used herein.

The nucleic acid molecules of the present invention such as those described above can be generated using standard molecular biology techniques, and sequence information of known EGF encoding nucleic acid molecules (e.g., EGF nucleic acid and polypeptide sequences from mammalian species, such as human and mouse, can be found in nucleic acid databases such as GenBank and SWISS-PROT). For example, nucleic acid molecules can be amplified and isolated by the polymerase chain reaction using synthetic oligonucleotide primers designed based on one or more of the nucleic acid sequences provided herein and/or the complement of those sequences. See generally PCR Technology: Principles and Applications for DNA Amplification (ed. H. A. Erlich, Freeman Press, NY, N.Y., (1992); PCR Protocols: A Guide to Methods and Applications (Eds. Innis et al., Academic Press, San Diego, Calif., (1990); Mattila et al., *Nucleic Acids Res.*, 19:4967 (1991); Eckert et al., *PCR Methods and Applications*, 1:17 (1991): PCR (eds. McPherson et al., IRL Press, Oxford)); and U.S. Pat. No. 4,683,202.

Other suitable amplification methods include the ligase chain reaction (LCR) (See Wu and Wallace, *Genomics*, 4:560 (1989), Landegren et al., *Science*, 241:1077 (1988)), transcription amplification (Kwoh et al., *Proc. Natl. Acad. Sci. USA*, 86:1173 (1989)), and self-sustained sequence replication (See Guatelli et al., *Proc. Nat. Acad. Sci. USA*, 87:1874 (1990)) and nucleic acid based sequence amplification (NASBA). The latter two amplification methods involve isothermal reactions based on isothermal transcription, that produce both single stranded RNA (ssRNA) and double stranded DNA (dsDNA) as the amplification products in a ratio of about 30 or 100 to 1, respectively.

Another aspect of the present invention pertains to nucleic acid constructs containing a nucleic acid molecule described herein. The constructs comprise a vector (e.g., an expression vector) into which a sequence of the invention has been inserted in a sense or antisense orientation. As used herein, the term "vector" or "construct" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombination expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, "Gene Expression Technology: Methods in Enzymology" 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences).

It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells, such as E. coli, insect cells (using baculovirus expression vectors), yeast cells or mammalian cells. Suitable host cells are discussed further in Goeddel, (supra). Alternatively, the recombinant expression vector can be transcribed and translated in vitro, for example, using T7 promoter regulatory sequences and T7 polymerase.

Another aspect of the invention pertains to host cells into which a recombinant expression vector of the invention has been introduced. The terms "host cell" and "recombinant host cell" are used interchangeably herein: It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., E. coli), insect cells, yeast, or mammalian cells (such as Chinese hamster ovary cells (CHO) or COS cells, human 293T cells, HeLa cells, NIH 3T3 cells, and mouse erythroleukemia (MEL) cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecules (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the nucleic acid of interest. Preferred selectable markers include those that confer resistance to drugs, such as G418, hygromycin, or methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

Pharmaceutical Compositions

The present invention also pertains to pharmaceutical compositions comprising the polypeptides and/or nucleic acid molecules described herein. For instance, a polypeptide or a nucleic acid molecule or a nucleic acid construct (vector) comprising a nucleotide of the present invention can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylase or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g. lubricants, preservatives, stabilizers, wetting agents, emulsifiers, salts for influencing osmotic pressure, buffers, coloring, flavoring and/or aromatic substances and the like that do not deleteriously react with the active agent in the composition (i.e., a polypeptide and/or nucleic acid molecule of the invention).

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devices ("gene guns") and slow release polymeric devices. The pharmaceutical compositions of this invention can also be administered as part of a combinatorial therapy with other compounds.

The polypeptides and/or nucleic acid molecules of the present invention can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound (polypeptide and/or nucleic acid). Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The polypeptide and/or nucleic acid molecule may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

The polypeptides and/or nucleic acid molecules described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The polypeptides and/or nucleic acid molecules are admininstered in a therapeutically effective amount. The amount of polypeptide and/or nucleic acid molecule that will be therapeutically effective in the treatment of a particular disorder or conditions will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of the disease or condition, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the polypeptide and/or nucleic acid molecule of the present invention can be separated, mixed together in any combination, present in a single vial or tablet. Compositions assembled in a blister pack or other dispensing means is preferred. For the purpose of this invention, unit dosage is intended to mean a dosage that is dependent on the individual pharmacodynamics of each composition and administered in FDA approved dosages in standard time courses.

Methods of Therapy

The present invention also pertains to methods of treatment (prophylactic, diagnostic, and/or therapeutic) for a conditions characterized by EGF biological activity. A "condition characterized by EGF biological activity" is a condition in which the presence of EGF polypeptide is therapeutic. Such conditions include wound healing, corneal growth and differentiation, and conditions involving pathologic changes of gastric mucosa, and the treatment involves using a polypeptide of the present invention or a nucleic acid molecule encoding such a polypeptide. More than one polypeptide or nucleic acid molecule of the present invention can be used concurrently, if desired.

The term "treatment" as used herein, refers not only to ameliorating symptoms associated with the disease or condition, but also preventing or delaying the onset of the disease, and also lessening the severity or frequency of symptoms of the disease or condition. The therapy is designed to enhance, replace, or supplement activity of a wild-type EGF polypeptide in an individual. For example, a polypeptide and/or nucleic acid molecule of the present invention can be administered in order to increase the expression or availability of polypeptide having epidermal growth factor biological activity. Up-regulation or increasing expression or availability of a polypeptide of the present invention could compensate for the expression or activity of a defective gene in an individual that cause insufficient amounts of EGF, or an EGF polypeptide with decreased biological activity to be produced.

The therapeutic compound(s) or the present invention are administered in a therapeutically effective amount (i.e., an amount that is sufficient to treat the disease or condition, such as by ameliorating symptoms associated with the disease or condition, preventing or delaying the onset of the disease or condition, and/or also lessening the severity or frequency of symptoms of the disease or condition). The amount that will be therapeutically effective in the treatment of a particular individual's disease or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or condition, and should be decided according to the judgment of a practitioner and each patient's circumstances. Effective doses may be extrapolated from dose-response curves derived from in vitro or animal model test systems.

The therapeutic compounds of the present invention can be used, either alone or in a pharmaceutical composition as described above. For example, a polypeptide or nucleic acid of the present invention, either by itself or included within a vector, can be introduced into cells (either in vitro or in vivo) such that the cells produce the desired polypeptide. If desired, cells that have been transformed with the nucleic acid molecule of the present invention can be introduced (or re-introduced) into an individual affected with the disease. Thus, cells that, in nature, lack EGF biological activity or for which increased EGF biological activity is desirable can be engineered to express the desired polypeptide.

Other gene transfer systems, including viral and nonviral transfer systems, can be used. Alternatively, nonviral gene transfer methods, such as calcium phosphate coprecipitation, mechanical techniques (e.g., microinjectin); membrane fusion-mediated transfer via liposomes; or direct DNA uptake, can also be used to introduce the desired nucleic acid molecule into a cell.

Exemplification

EXAMPLE 1

Assay for EGF Receptor Binding

Competent bacterial cells were transformed with mutant EGF polypeptides using standard transformation techniques and colonies were picked off plates and transferred into individual wells of 96 well microtiter plates. The cells were then incubated under conditions suitable for growth and secretion of the h/mEGF polypeptides (EGF variants).

The cell supernatants, containing the secreted EGF variants, were separated from the bacterial cells and evaluated for activation of the EGF receptor, using standard methods. Kits for assaying EGF receptor activity are commercially available. One of the EGF variants that showed EGF receptor activation activity was a variant termed EGF0021. The amino acid sequence of EGF0021 is shown in FIG. 2. The gene encoding EGF0021 (shown in FIG. 3; SEQ ID NO: 3) was cloned into an expression system such that the EGF0021 polypeptide was labeled with a His-tag, using standard recombinant DNA techniques. The His-tagged EGF0021 polypeptide was then purified using standard purification methods for use in additional analyses.

Figure 4B:
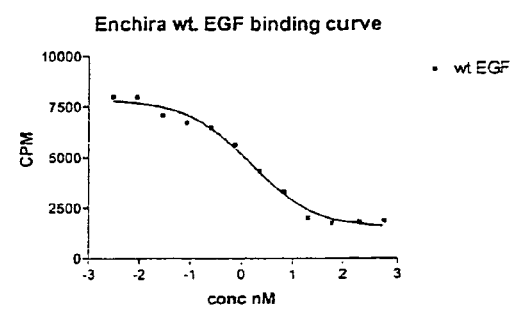
FIG. 4B is a graph of the displacement of $^{125}$I labeled-EGF from EGF receptors (counts per minute (cpm)) by various concentrations of human wild-type EGF, purified in-house A(log [conc. nM]).
Figure 4C:
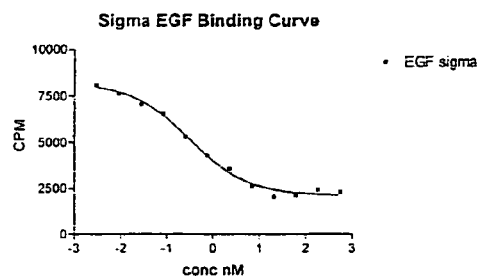
FIG. 4C is a graph of the displacement of $^{125}$I labeled-EGF from EGF receptors (counts per minute (cpm)) by various concentrations of human wild-type EGF obtained from Sigma Chemicals, St. Louis, Mo.) (log [conc. nM]).

The binding activity of the purified EGF0021 polypeptide was compared to the binding activity of human wild-type EGF polypeptide using a standard binding competition assay (displacement of $^{125}$I-EGF from the EGF receptor). These EGF receptor binding competition assays were carried out by measuring the displacement of $^{125}$I-EGF from the EGF receptor in the presence of increasing amounts of EGF0021, human wild-type EGF purified in-house using standard methods, or human wild-type EGF commercially obtained from Sigma Chemicals (St. Louis, Mo.). The results of these competitive assays are shown in FIGS. 4A (EGF0021) FIG. 4B (human wild-type EGF purified in-house) and FIG. 4C (human wild-type EGF from Sigma Chemicals). The calculated EC50s of the competitive binding assays using human wild-type EGF produced in-house and human wild-type EGF from Sigma Chemicals were approximately the same, at 1.542 nM and 0.318 nM, respectively. The calculated EC50 of the competitive binding assay using EGF0021, however, was substantially higher, with an EC50 of 145.2. These data indicate that the EC50 for EGF0021 is about two orders of magnitude higher than the wild-type forms of hEGF.

EXAMPLE 2

Assaying EGF Receptor Binding Activity

Figure 5A:
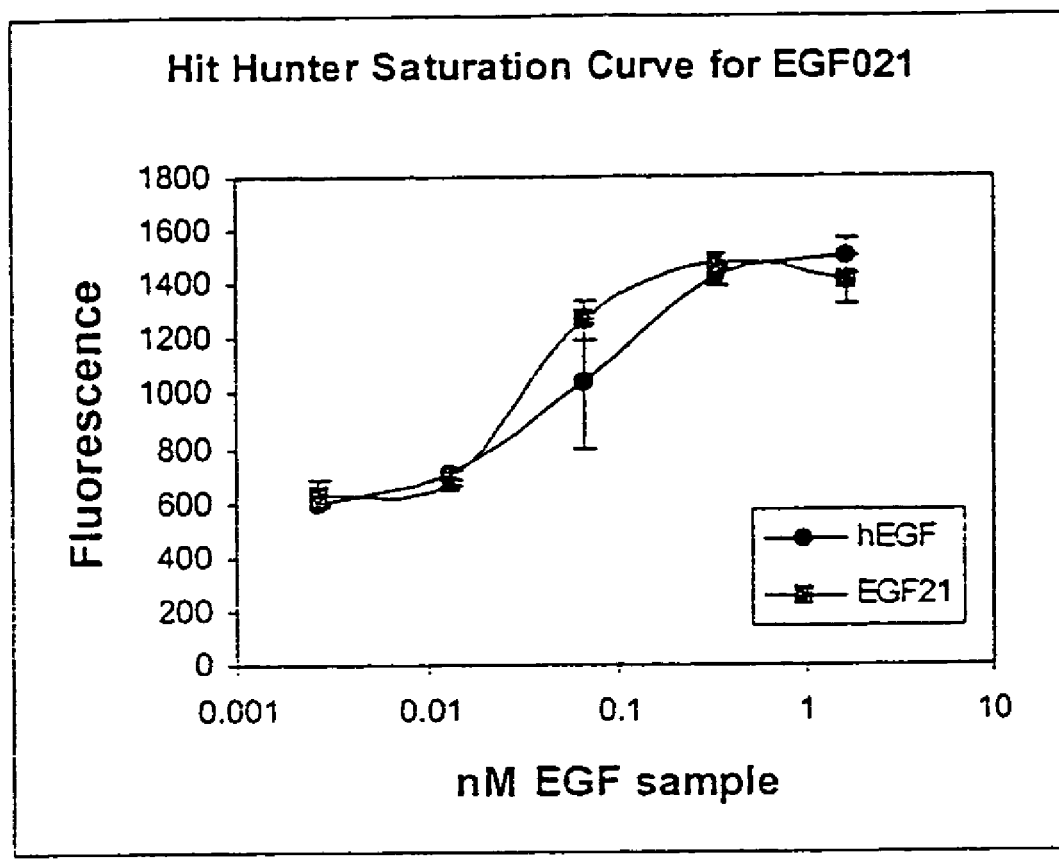
FIG. 5A is a graph of the activity of EGF receptors (measured by quantifying enzyme linked activity (fluorescence)) when stimulated with various concentrations of EGF0021 (■) or human wild-type EGF (•) polypeptide. Each point is an average±the standard deviation of 3 samples.

The activity of the EGF receptor upon binding by purified EGF0021 protein was compared to the activity of the EGF receptor upon binding by human wild-type EGF using an in vitro kinase assay. The receptor activity was measured using a HitHunter kit, according to the manufacturer's instructions (Discoverx, Freemont, Calif.). This assay measured beta-galactosidase activity (fluorescence) as a read-out of the EGF receptor activity. This assay was first performed using 1 μL of A431 cell membrane preparation per assay (the membrane preparation contains EGF receptors), and either EGF0021 or human wild-type EGF (HEGF) at concentrations ranging from about 0.001 nM about 10 nM. The results of this assay are shown in FIG. 5A, and indicate that under these assay conditions, both human wild-type EGF and EGF0021 have nearly the same activity.

Figure 5B:
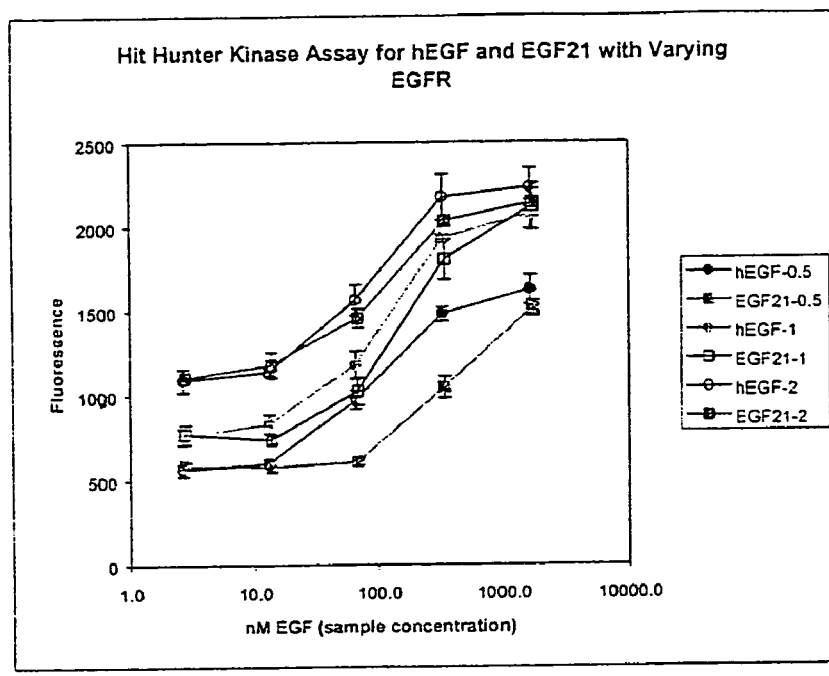
FIG. 5B is a graph of the activity (measured by quantifying enzyme linked activity (fluorescence)) of EGF receptors (contained in a 0.5 µL, 1.0 µL, or 2.0 µL sample of an A431 membrane preparation) by various concentrations of human wild-type EGF or EGF0021 (nM EGF sample concentration) polypeptide.

The HitHunter component of the assay was further examined to determine if it was limiting the ability to measure the kinase $V_{max}$ in the assay. As discussed above, receptor activity was first assessed using 1 μL of A431 cell membrane preparation per assay. In a subsequent experiment, the amount of A431 membrane preparation was varied such that 0.5 μL, 1.0 μL or 2.0 μL of membrane preparation was used to carry out the assay using either EGF0021 or wild-type hEGF as the EGF receptor ligand. The results of this study are shown in FIG. 5B, which is a graph of the fluorescence indicating beta-galactosidase activity (a read-out of receptor activity). upon exposure to increasing amount of EGF0021 or wild-type HEGF, assayed with varying concentrations of membrane preparation. The observation that both wild-type HEGF and EGF0021 reached maximal activity at the same point with either 1.0 µL or 2.0 µL of membrane preparation indicates that some aspect of HitHunter is limiting. With 0.5 µL of membrane preparation, wild-type HEGF appeared to be leveling out at approximately 100 nM, but EGF0021 contained to rise in a linear fashion. Still lower amounts of membrane preparation may be necessary to determine the EC50 in this assay or to demonstrate the maximum differences in $V_{max}$ supported by wild-type HEGF and EGF0021. But, these data suggest that EGF0021 is a super agonist (e.g., EGF0021 can activate the EGF receptor at lower levels of binding compared to human wild-type EGF and can activate the kinase to a higher $V_{max}$ at saturation).

EXAMPLE 3

Activity of EGF0021 in Cell Proliferation Assays

Figure 6A:
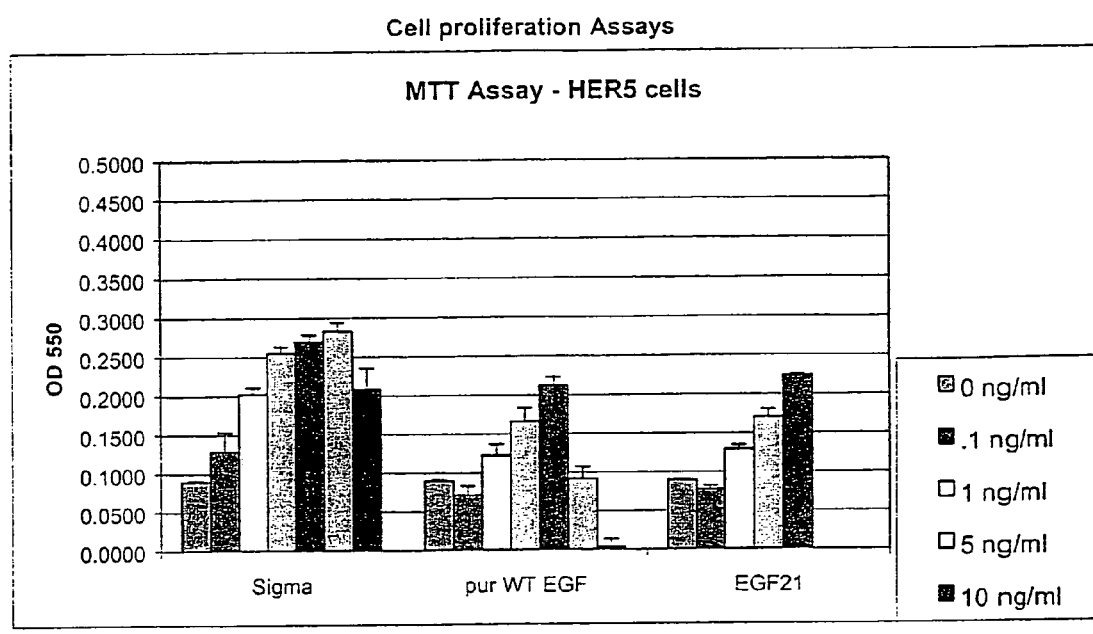
FIG. 6A is a histogram of the effects of various concentrations of human wild-type EGF obtained from Sigma Chemicals (Sigma), human wild-type EGF purified in-house (pur WT EGF) and EGF0021 (EGF21) on the proliferation of HER5 cells (measured as absorbance of light at 550 nm (OD 550).
Figure 6B:
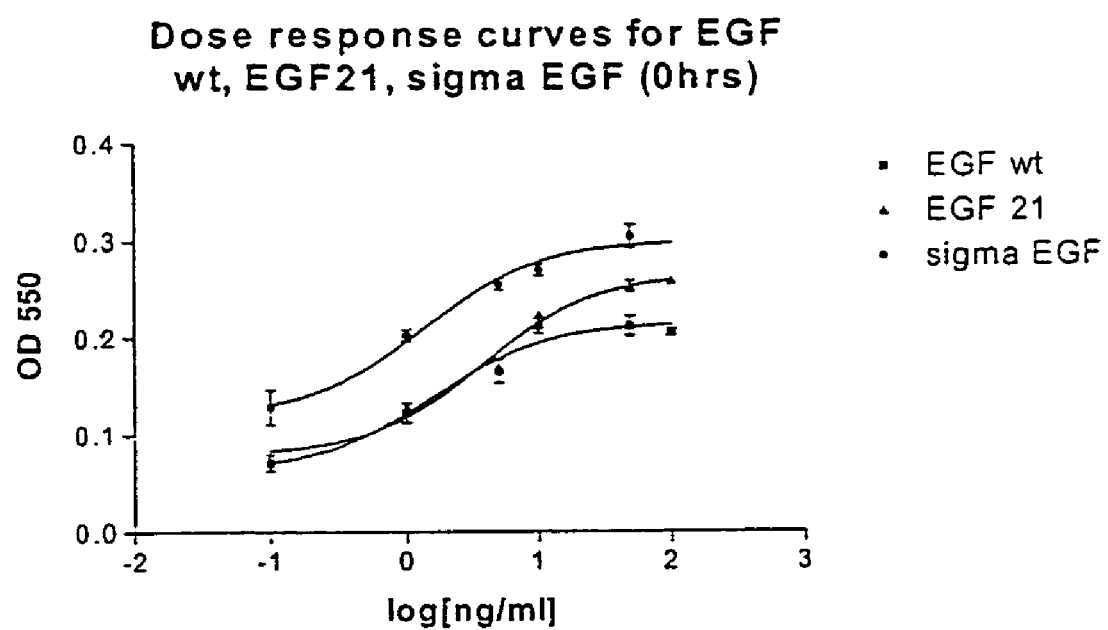
FIG. 6B is a graph of the effects of the log of various concentrations (ng/mL) of human wild-type EGF obtained from Sigma Chemicals (Sigma EGF), human wild-type EGF purified in-house (EGF wt) and EGF0021 (EGF 21) on the proliferation of HER5 cells (measured as absorbance of light at 550 nm (OD 550)).

The purified EGF0021 polypeptide was compared to human wild-type EGF in a cell proliferation assay. This standard assay measures the rate of growth of a cell line (HER5) that is dependent on extracellular EGF to stimulate growth. Cell proliferation is measured by detecting the number of metabolically active cells (by measuring cleavage of the yellow tetrazolium salt MTT to purple formazan crystals that are solubilized and spectrophotometrically quantified using an ELISA reader). Cell proliferation MTT kits are commercially available, for example, from Roche Applied Science (Indianapolis, Ind.). In this cell proliferation assay, HER5 cells were exposed to 0 ng/mL, 0.1 ng/mL, 1 ng/mL, 5 ng/mL, or 10 ng/mL of each of human wild-type EGF obtained from Sigma Chemicals, human wild-type EGF purified in-house, and EGF0021, and the cells were incubated for a period of time. At the end of the assay, the cells were assayed for proliferative activity as described above. The results of this assay are shown in FIG. 6A, which is a histogram of the OD 550 (indicating level of proliferative activity) for cells exposed to each of the conditions described above. This same data is graphed as the OD 550 versus the log of the concentration of human wild-type EGF obtained from Sigma Chemicals, human wild-type EGF purified in-house, and EGF0021 in FIG. 6B. As discussed above, and shown in FIGS. 4A–4C, the binding affinity of EGF0021 for the EGF receptor is approximately 100 times lower than the binding affinity of human wild-type EGF for the EGF receptor. Yet despite this lower binding affinity, the cells administered EGF0021 showed cell proliferation activity that was similar to the cell proliferation activity of cells administered human wild-type EGF (FIG. 6). Together, these data indicate that the EGF0021 is about 150 times more active than human wild-type EGF on a molar basis. These data indicate that EGF0021 promotes cell proliferation activity. Thus EGF0021 can be used to promote cell proliferation in therapeutically useful situations, such as those situations where EGF is indicated (e.g., would healing, corneal regeneration, and repair and/or maintenance of the gastrointestinal tract.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated epidermal growth factor polypeptide comprising the amino acid sequence of SEQ ID NO: 2.

\* \* \* \* \*

SEQUENCE LISTING

<160> NUMBER OF SEQ ID NOS: 3

<210> SEQ ID NO 1
<211> LENGTH: 53
<212> TYPE: PRT
<213> ORGANISM: homo sapien

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Artificial Sequence
<220> FEATURE:
<223> OTHER INFORMATION: syntheic

<400> SEQUENCE: 2

Asn Ser Asp Ser Gly Cys Pro Ser Phe His Asp Gly Tyr Cys Leu Asn
1               5                   10                  15

-continued

```
Gly Gly Val Cys Met Tyr Ile Glu Ala Leu Asp Lys Tyr Ala Cys Asn
         20                  25                  30
Cys Val Ile Gly Tyr Asn Gly Asp Arg Cys Gln Thr Arg Asp Leu Lys
         35                  40                  45
Trp Trp Glu Leu Arg
         50

<210> SEQ ID NO 3
<211> LENGTH: 159
<212> TYPE: DNA
<213> ORGANISM: Artificial Sequence
<220> FEATURE:
<223> OTHER INFORMATION: synthetic

<400> SEQUENCE: 3
aatagtgatt ctggatgtcc ctcgttccat gatgggtact gcctcaatgg tggtgtgtgc    60
atgtatattg aagcattgga caagtatgca tgcaactgtg ttattggcta caacggggat   120
cgatgtcaga ctcgagacct gaagtggtgg gaactgcgc                          159
```